United States Patent [19]

Harris et al.

[11] Patent Number: 4,765,737
[45] Date of Patent: Aug. 23, 1988

[54] CELL SIZE MEASUREMENTS USING LIGHT IN FLOW CYTOMETRY AND CELL SORTING

[75] Inventors: William V. Harris, Interlaken; Bruce R. Land, Trumansburg, both of N.Y.

[73] Assignee: Cornell Research Foundation, Ithaca, N.Y.

[21] Appl. No.: 31,790

[22] Filed: Mar. 30, 1987

[51] Int. Cl.$^4$ ............................................. G01N 15/02
[52] U.S. Cl. ...................................... 356/336; 377/11; 356/73
[58] Field of Search ......................... 356/335, 336, 73; 377/11; 328/111, 115

[56] References Cited

U.S. PATENT DOCUMENTS

4,110,043  8/1978  Eisert .................................. 356/336

Primary Examiner—R. A. Rosenberger
Attorney, Agent, or Firm—Ralph R. Barnard

[57] ABSTRACT

In a flow cytometer where the laser beam is larger than the size of each biological cell of a column of cells being passed through the laser beam at a high rate wherein new and improved method and means are used to calculate the size of the cells as sensed by low angle forward light scatter or secondary emission of fluorescent material on the surface of the cell by measuring the time-of-flight of the smaller cell across the laser beam, with the time-of-flight being measured by integrating an electrical signal from either the forward light scatter or the secondary flourescent emission from a single cell as it passes through the laser beam and deriving still another electrical signal measuring the peak amplitude of the first signal and then dividing the integrated signal by the peak signal and subtracting a constant electrical signal from that quotient.

10 Claims, 3 Drawing Sheets

ERYTHROCYTES FROM 2N/3N MOSAIC PHLOXINUS

CELL SIZE MEASUREMENTS USING LIGHT IN FLOW CYTOMETRY AND CELL SORTING

The present invention relates generally to the field of cell flow cytometry using light measurement and cell sorting which includes the measurement of the size of selected cells, and more particularly with the making of the measurement of the size of the cell when the cell is the only cell passing at right angles through a light beam and the cross section of the light beam is larger than the cell size to be measured.

There are many publications relating to the measurement of sizes of cells in the field of flow cytometry and cell sorting. As the field of biotechnology expands, the application to biological cells will be manifold.

An article by J. A. Steinkamp and H. A. Crissman in the *Journal of Histochemistry and Cytochemistry*, Vol. 22, No. 7, pp. 616–621 (1974) entitled "Automated Analysis of Deoxyribonucleic Acid, Protein and Nuclear to Cytoplasmic Relationships in Tumor Cells and Gynecologic Specimans" is representative of the prior art. In that publication, cells to be analyzed are stained with fluorescent material and passed in a stream through a laser beam at right angles where both low angle forward scatter of light and fluorescent emmissions are measured at right angles from both the axis of flow and the laser beam. Red and green fluorescent signals are amplified and then integrated by electronic integrators to provide an output signal with an amplitude proportional to total DNA and protein content respectively. One color measured DNA and the other color measured protein content. The integrators contained additional circuitry to detect the time duration in which fluorescence signals were above a threshold level (i.e. cross-over timing). These time spans were then converted to signal amplitudes which are proportional to nuclear and cytoplasmic diameters using time-to-voltage height converters. Steinkamp describes his system as another technique for determining nuclear and cytoplasmic size relationships of cells stained with two fluorochromes specific to the nucleus and cytoplasm. He calls his technique "time of flight" as measuring the time it takes for the cell nucleus and cytoplasm to cross through a narrow laser beam. He states that if the cell flow rate (velocity) is constant, then the nuclear and cytoplasmic diameters are proportional to the time of flight across the beam. He concludes that a new methodology is demonstrated in which the duration of time of flight across a narrow laser beam is used to determine nuclear and cytoplasmic sizes and that improvements in laser beam shaping optics are being incorporated into the system to provide even narrower beams to measure cell dimensions more accurately.

Later, an article by T. K. Sharpless and M. R. Melamed in the *Journal of Histochemistry and Cytochemistry*, Vol. 24, No. 1, pp 257–264 (1976) entitled "Estimation of Cell Size from Pulse Shape in Flow Cytofluorometry" confirms that as long as the beam of light traversed by the cell is not broad compared to the cell diameter, the time course of fluorescence emission will be a blurred one-dimensional image of the cell and from such an image one might expect at least a good approximation of cell size. Moreover, the publication goes on to describe two alternate amplitude-independent estimates of pulse width. The first is based on a threshold at some fraction of pulse height, or on a pair of thresholds scaled to some fixed central fraction of the total intensity. The second is based on the ratio of pulse area to peak height. Both of these methods require that the pulse shape be stored in a high quality delay line until the peak height or total intensity has been measured and held.

Later, a textbook was published by Wiley & Sons, Inc. (1979) entitled *Flow Cytometry and Sorting* and edited by Melamed et al. Chapter 6 of that book entitled "Slit-scanning and Pulse Width Analysis" by Leon L. Wheeless, Jr. is pertinent background to the teaching of the present invention in that it examines and reinforces the custom and practice of using the benefits of the narrow laser beam requirements for the measurement of the size of cells in flow cytometry equipment wherein the phrase one-dimensional slit-scan system is used to characterize the narrow laser beam impinging on the path of flowing cells at right angles and the course of either the forward light scatter signal or the fluorescence emmission is a blurred one dimensional image of the cell being measured. Based on the technique described in Chapter 6, laser resolution slit-scan systems are widely used in present day cell flow cytometry and cell sorting systems, and narrow laser beams (when compared with the size of the cells being measured) are widely used as an accepted technique. This is true despite the fact that the use of the narrow laser beam gives rise to significant disadvantages. They are: (1) The construction of and maintenance of the very narrow beam is critical to the operation of the equipment; (2) The narrow laser beam is applied to only a small fraction of each cell at any one time, and the light scatter or secondary light emission from the fluorescent material on the cell does not depict the nature of the cell with fidelity without the use of additional electronic circuitry including a high quality delay line for the purpose of piecing the signal from plural cross sections of the cells together as required for the measurement of, or sampling of, the total cell under inspection; (3) When the aforesaid additional electronic circuitry, including an electronic delay line and computational devices and or circuits, are used, the output signal from either the forward light scatter detection or the secondary emission detectors cannot be used to initiate the sorting function for each cell of the stream as it passes beyond the flow chamber unless the number of cells passing through the laser in the stream per unit time is relatively low. For example, when the electronic delay lines and the resulting computational complexity are made necessary by the use of the narrow laser beam, the maximum rate of introduction of stained cells into the stream through the flow chamber is about 1000/sec, thereby placing great limitations on the operation of the equipment and particularly the sorting operation.

On the other hand, dropping the electronic delay time from the operating system and relying on a signal from forward light scatter or secondary fluorescent emission from a part of a cell was not acceptable as a basis for sorting (size or other parameters) unless all parts of each of the cells were uniform in their optical characteristics or their fluorescence.

When Becton Dickinson, Inc. of Mountainview, Calif., designed its Fluorescence Activated Cell Sorter, Model 440, it clearly decided to market a piece of equipment which would sort a stream of cells one at a time at a stream rate of up to 5000 cells per second. Therefore, the complications and limitations arising out of narrow laser beams were not acceptable. In fact, the cell size limits for the operation of the FACS 440 is the range from 2u (microns) to 30u, and the laser beam is designed to have a larger cross section of 50u. As the cell passes through the larger beam, the system measures both front scatter of the laser beam light energy as the cell passes through the beam, as well as orthogonal secondary emissions from the cell during that time reflecting characteristic fluorescence from the cell and its nucleus as desired. The method used for measuring cell size under these circumstances, if any, is to assume that the amplitude of the forward light scatter by the cell is directly proportional to cell size and a cell sorting signal is selected as a measure of the amplitude. The amplitude of the forward light scatter signal can only approximate the cell size when the cells do not vary from cell to cell in their spectral characteristics. It is impossible to determine whether a decreased peak scatter signal is the result of smaller size or light absorption of the cell or particle. The amplitude of the signal derived from the secondary emission from fluorescence from the cell or its nucleus similarly lacks accuracy as a measure of the size of the cell and its nucleus because the peak amplitude reflects only the amount of fluorochrome. The system included no functional capability to accurately measure the size of each cell in the stream and sort on that information.

The present invention was made in the circumstance that the present inventor had a Model 440 Fluorescent Activated Cell Sorter with all of the benefits of the laser beam being larger than the cells and a high operating rate well in excess of 1000 cells/sec but no accurate capability to measure size of the cell passing through the laser beam, as well as sort the cells one from another, based on the size measurements. The size of the cells being smaller than the cross section laser beam allowed the cell to be examined as to front scatter and secondary emission in total and not in segments. The time of flight measurement described in the three different scientific papers described herein above identified the measurement of the time it took for a cell (whose size is to be measured) nucleus or cytoplasm to cross through a narrow laser beam. The problem solved by the present invention is to measure the size of a cell by measuring its time of flight passing through a beam which is larger than the cross section of the cell because in that context the cell can be examined in total as well as provide "immediate" information as to the size for recording and/or sorting.

It is a primary object of the present invention to provide a new and improved method for measuring the size of a cell flowing at a constant velocity by measuring its time of flight at a right angle through a light beam which is larger in cross section than the cross section of the flowing cell.

It is another object of the present invention to provide a new and improved method for measuring the size of a cell flowing in a column forming a stream of plural cells at a constant velocity by measuring the cells' time of flight at a right angle, one cell at a time, through a light beam which is larger than the cross section of each of the flowing cells so that each of the cells can be examined in total and provide immediate information as to size for recording and/or sorting.

It is still another object of the present invention to provide a new and improved method for measuring the size of a cell flowing in a column as a stream of plural cells at a constant velocity by measuring its time of flight at a right angle one cell at a time through a light beam which is larger than the cross section of each of the flowing cells so that each of the cells can be examined in total by the low angle forward light scatter in the direction of flow and/or the secondary emmission from the fluorescent material on the surface of the cell as seen from a direction which is orthogonal to the direction of flow of the column of cells and the light from the cells to provide immediate information as to the size of each cell for recording and/or sorting.

It is another object of the present invention to provide a new and improved method for measuring the size of a cell flowing in a column in a stream of plural cells at a constant velocity by measuring its time of flight at a right angle one cell at a time through a light beam which is larger than the cross section of each of the cells such that each cell can be examined in total by the low angle forward light scatter to provide immediate information as to the size of the cell for recording and/or sorting and the flow rate of the cells through the light beam is substantially in excess of 1,000 cells/sec.

It is another object of the present invention to provide a new and improved method for measuring the size of a cell flowing in a column in a stream of plural cells at a constant velocity by measuring its time of flight at a right angle one cell at a time through a light beam which is larger than the cross section of each of the cells such that each cell can be examined in total by the secondary emmission from the fluorescent material on the surface of the cell as seen from a direction which is orthogonal to the direction of flow of the column of cells and the light beam to provide immediate information as to the size of each cell for recording and/or sorting at a flow rate of the cells through the light beam is substantially in excess of 1,000 cells/sec.

The teachings and objects of the present invention are provided by utilizing the following new and improved method of measuring the size of a biological cell in a flow cytometer, including a new combination of electrical circuitry means for producing the same:

1. Directing said biological cells in column flow at a constant velocity;

2. Passing a laser beam having a cross section larger than each of said cells through said biological cells in column flow so that only one biological cell passes through said laser beam at a time;

3. Measuring the time of flight of each said biological cell through said laser beam deriving an electrical signal commensurate with the width and/or volume of each said biological cell;

4. The steps of measuring the time of flight of each of said biological cells through said laser beam comprising the following steps:
   a. deriving a first electrical signal from the low angle forward light scatter characteristic or secondary fluorescent emission from a single cell as it passes through the said laser beam;
   b. deriving a second electrical signal having an amplitude determined by the time integral of said first electrical signal;
   c. deriving a third electrical signal having an amplitude equal to the peak amplitude of said first electrical signal;
   d. deriving a fourth electrical signal by dividing the said second electrical signal by the said third electrical signal therefore deriving an electrical signal commensurate with the width of each said biological cell plus the width of the laser beam.
   e. deriving a fifth electrical signal by subtracting from said fourth electrical signal a constant electrical signal proportional to the width of the laser beam whereby the fifth electrical signal is directly proportional to the width of said biological cell.

The fifth electrical signal may then be used to initiate a sorting operation at a cell flow rate substantially in excess of 1,000 cells/sec. Moreover, when the fifth signal is raised to the third power, the magnitude thereof is directly proportional to the volume of each of said biological cells and/or its nucleus.

As will be clear as this description proceeds, the method of measuring the size or diameter of biological cells in accordance with the teachings of the present invention may be used in either or both of the (lower angle) front light scatter channels or orthogonal secondary fluorescent emission channels. The orthogonal secondary fluorescent emission channel may use the teachings of the present invention simultaneously in two separate channels to simultaneously measure the size (diameter) of the nucleus and the cytoplasm of the same biological cell. As known in the prior art, different colored fluorescent materials are used to stain the nucleus of a cell as distinguished from the fluorescent material which is used to stain the whole cytoplasm of the same cell.

Figure 1:
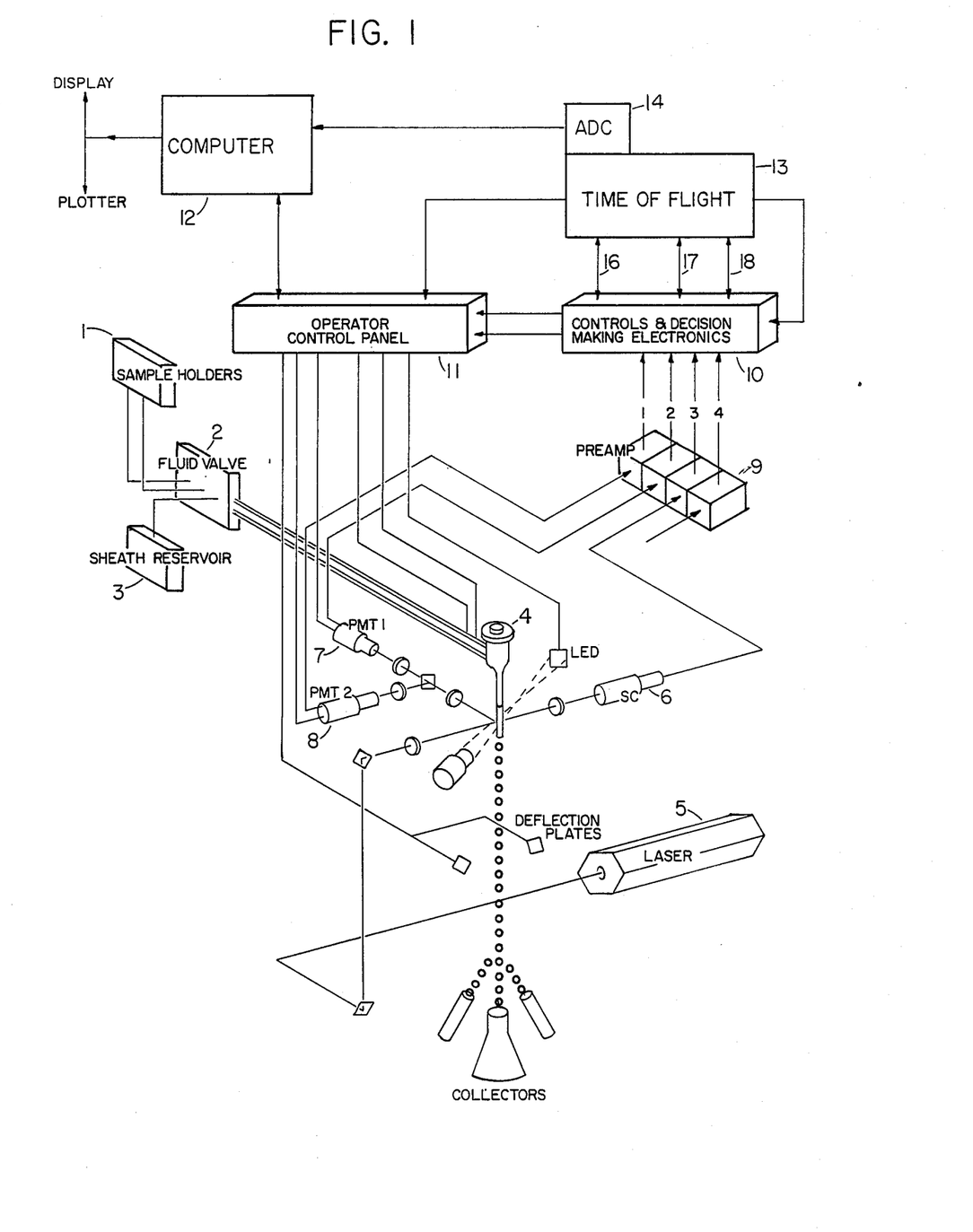
FIG. 1 is a simplified block diagram showing a laser cell sorter including fluorescent activation channels of the type that could benefit from modification to practice the teachings of the present invention, but it does not show that portion of the system which would necessarily be modified.

Referring to FIG. 1, the simplified diagram shows the elements of a typical flow cytometer and biological cell sorter present in a Becton Dickinson FACS 440 Laser Cell Sorter. The equipment and technical manual for the product is available for sale and is relatively widely sold in the United States and perhaps elsewhere. The Technical Manual is also on the shelf of the Library of the College of Veterinary Medicine, Cornell University, in Schurman Hall, and is available for reading and copying. The components of the FACS laser cell sorter as shown in FIG. 1 for placing the stream of cells to be measured on a path through a laser beam one cell at a time at a constant velocity is illustrative of such equipment in wide usage in this country.

Cells are injected into the sorter of a flowing stream of compatable sheath fluid establishing a laminar coaxial flow within a nozzle-transducer assembly with selected supporting components. Block 1 is a cell sample container. Block 2 is a sheath fluid container. The contents of both containers in combination with a suitably adjusted pressure source of air interact with a fluid valve asssembly in container 3 to provide a sample of cells for measurement which may be fluorescently tagged with the cells being in the center of a flowing stream of a compatable sheath fluid. Thus, a laminar (nonturbulent) coaxial flow of cells in a fluid sheath is established within nozzle-transducer assembly 4. This coaxial flow will constrain the sample fluid and cells contained therein to the central portion of the liquid flow stream, insuring that at all times cellular material is prevented from touching the nozzle assembly and that the system is comparatively free of contamination and blockages. Sheath and sample liquids may be maintained at a selected constant temperature. The cells in the stream move one by one down through the nozzle-transducer assembly 4 at a constant velocity (e.g., about 10 meters per sec), passing through a 50 micron laser beam directed as shown. The stream, after emerging from the nozzle tip, is about 50 microns in diameter, and continues in an unbroken jet for a few millimeters, after which perturbations within the flow stream, induced by means of a 40 kHz piezoelectric transducer upon which the nozzle is mounted, build up and cause the stream to break up into well-defined, precisely located, constant volume droplets. Immediately below the nozzle (not separately shown in assembly 4) and before forming into droplets, the stream is interrogated by a laser beam to ascertain the presence of cells and their characteristics.

As cells pass through the laser beam, different cells give different but characteristic signals in the low angle forward scatter pattern, varying in the intensity of the light corresponding to each cell. These signals are converted into electrical pulses of varying amplitudes by the photodetectors in the form of a forward scatter collector 6.

Specifically, the scatter signal is detected by observing the illumination in the forward direction; that is, by looking at the cell when it is in line with and directly in front of the source, the laser beam. The intense, direct light from the laser is prevented from entering the scatter channel optics by means of an external obscuration. This type of scatter observation, called low angle forward light scatter, gives by far the largest signal from the cells being observed. In the cell sorter, the scatter signal can be observed over a wide angle—up to about 10° on either side of the laser beam, or over a low angle—down to 2° or 3° on either side of the beam. Wide-angle scattering does not have the significance in describing the benefits of the present invention, as does the low angle forward light scatter. Low-angle detection is dependent partly upon the cell or particle cross-sectional area, but also depends upon its refractive index relative to the medium in which it is immersed, and its optical density. Thus the held peak does not accurately measure size.

The fluorescence characteristics of the cell may be determined simultaneously with the scatter signal. The low angle forward scatter signal is always generated from a detectable cell, whereas a fluorescence signal may or may not be present, depending on cell characteristics. Cells that have been tagged by means of a suitable fluorescent material can be detected by means of their emission when excited by the high-intensity light from the laser.

In the cell sorter, using typical biological fluorochromes, excitation occurs in the blue/green region, and reradiation, or fluorescence, occurs in the green/red region of the spectrum. This frequency shift allows the use of selective optical filters to eliminate unwanted signals due to scattering, diffraction, etc., within the flow stream, and permits a cell to be identified solely on the basis of its affinity to the fluorescent tagging material.

The cell sorter, such as the Becton Dickinson 440, may have additional lines in the ultraviolet region between 350 and 360 nanometers allowing the use of additional fluorochromes. The cell sorter may be provided with more than one fluorescence detectors (photomultiplier tubes). This permits double tagging of particular cells with different fluorochromes and measuring the uptake for each, thereby providing simultaneous measurement of more than one cell property.

In the description of the present invention, the two channels with different fluorescent properties are used to differentiate measurements made for a given cell between the nucleus and the cell plasma.

In passing through the laser beam, presence of a cell is detected by a characteristic scatter signal (which occurs at all times), and by one or two fluorescence signals (which may be generated). These optical signals are converted into electrical signals by suitable photo-detectors 6, 7, and 8, and the electrical signals are then processed by the electronics portion of the system.

Figure 2:
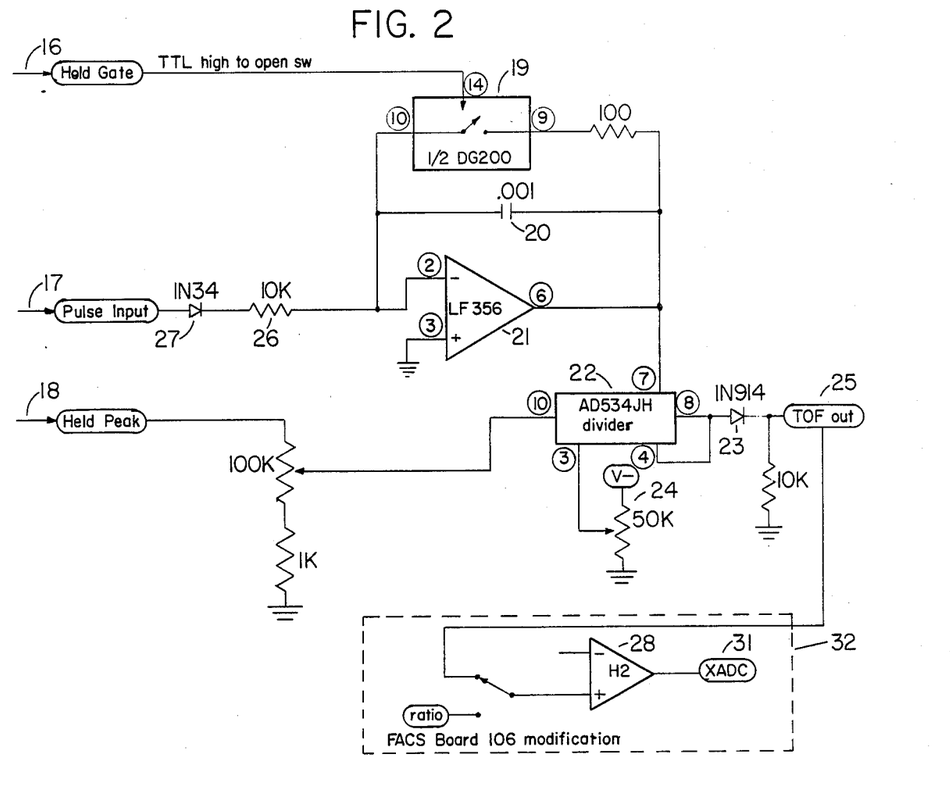
FIG. 2 is a simplified block diagram showing that part of a laser cell sorter of the type shown in FIG. 1 that would be modified to practice the teachings of the present invention.

The signals first pass through individual low-noise, variable-gain amplifiers 9, and then may be observed on an oscilloscope display (not shown) built into the instrument. From there they are passed to a part of the equipment that contains control and decision making electronics 10, which includes a pulse height analyzer. Block 11 of FIG. 1 contains the time-of-flight computational components which particularly distinguish the teachings of the present invention from the unaltered prior art Becton Dickinson FACS 440. FIG. 2 illustrates the time-of-flight computations which give rise to all of the advantages ennumerated herein.

In FIG. 2 there are three input lines from the pulse height analyzer portion of block 10 of FIG. 1 (the controls and decision making electronics for a fluorescent activated laser cell sorter of the Becton Dickinson FACS 440 type). The circuitry shown in this FIG. 2 is the additional or modified circuitry which is required beyond that in the original Becton Dickinson FACS 440 and which is required to practice the teachings of the present invention. If the teachings of the present invention were simultaneously utilized to measure cell size and/or sort by (1) measuring low angle forward light scatter, (2) measuring secondary emission from fluorescent tagging of the cell, and (3) measuring nucleus size of the cell by secondary emission of cell nucleus tagging as the cell passes through the larger laser beam, three circuits of the type shown in FIG. 2 would have to be used.

Figure 3:
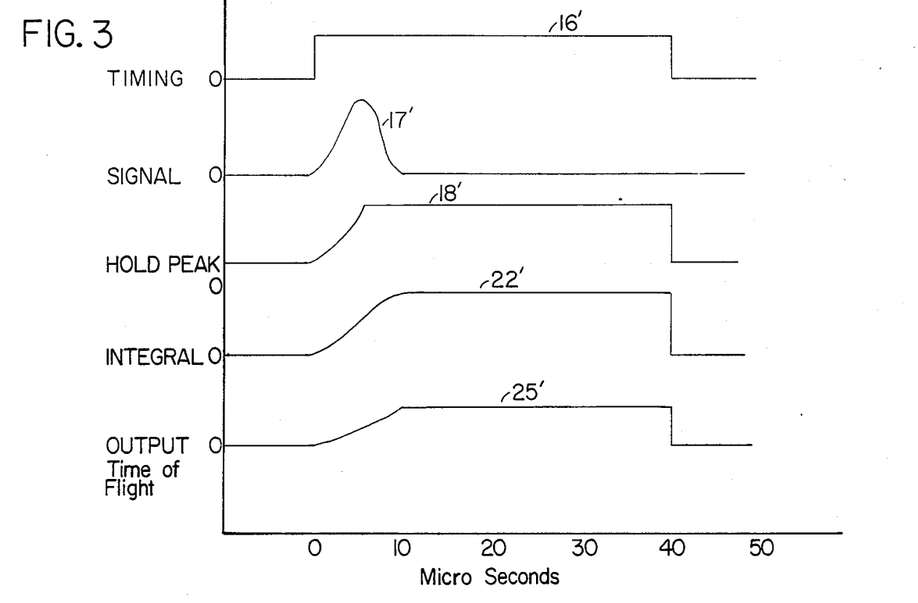
FIG. 3 shows the wave forms of many of the electrical signals derived by the electrical circuits of FIG. 2 in accordance with the teachings of the present invention.

FIG. 2 identifies the three input signals used to practice the teachings of the present invention (one timing gate and two related electrical analog signals). FIG. 3 shows the appropriate wave forms of those three input signals for the arithmetic computation provided by the cicuitry of FIG. 2 as it functions to measure cell size in accordance with the teachings of the present invention.

Referring to FIG. 2, input 16 is the timing voltage gate providing circuitry timing of the computation. In the Becton Dickinson FACS 440 this timing voltage gate is 40 microseconds in duration and is shown in the wave forms of FIG. 3. The timing voltage gate may be the same for the low angle forward light scattering mode in as well as a secondary emission from fluorescent tagging in modes when the rate at which the cells to be measured (passing one cell at a time through the larger laser beam) is 5,000 cells/sec. The time available for the computation of FIG. 2 and FIG. 3 to take place serially for every cell is 1/5,000 or 200 microseconds. FIG. 3 shows the computation of FIG. 2 as taking place in about 40 microseconds.

As the cell passes through the laser beam, the signal measured by forward scatter detector 6 appears as shown in FIG. 3 as a signal wave form 17' having an amplitude time relationship shown with the area under the curve representing the total light energy appearing in the low angle forward scatter envelope measured by detector 6. In FIG. 2 the terminal showing this input is identified as input 17. The standard circuitry of block 10 of FIG. 1 also provides as a standard calculation a signal wave form 18' commensurate with the highest voltage generated in the signal appearing at input 17. This signal is known as the held peak voltage signal and is applied to the circuitry of FIG. 2 by the electronics of block 10 on input line 18 of FIG. 2. These signals have been identified herein above in reference to the voltage generated by the light energy reaching scatter detector 6 of FIG. 1. On the other hand, the corresponding signals for the other modes of the circuitry of FIG. 2 when the signal 17 is representative of secondary emission from fluorescent tagging, which signal would appear in the outputs of either or both of two detectors shown in FIG. 1 as photomultiplier tubes 7 and/or 8. It is again emphasized the circuitry of FIG. 2 would have to be duplicated if a forward scatter signal and two secondary emission signals are processed simultaneously. Several of these signals may be logically combined to sort a single cell.

The detailed arithmetic operation in accordance with the teachings of the present invention is illustrated by the wave forms of FIG. 3 and is accomplished by the circuitry of FIG. 2. The system context of the arithmetic operation is, of course, set by all of the system components shown in both FIGS. 1 and 2. Referring again to FIG. 2, the 40 microsecond wave form 16' (FIG. 3) of the timing gate of terminal 16 is shown. The wave form 16' operates to initiate the opening of a conventional electronic switch 19, which is diagramatically shown in FIG. 2 as a mechanical switch such that it effectively places a capacitor 20 in parallel with an operational amplifier 21 such that the integrator formed by the operational amplifier and the capacitor and a resistor 26 is responsive to the pulse wave form 17' on input line 17, and that signal is integrated and appears at the terminal 22 as an input for an analog divider 23. The integrated pulse input signal is then applied to an analog divider 23, where it is then divided by the voltage signal representing the peak amplitude signal on line 18 of FIG. 2. The peak amplitude signal of wave form 18' is provided by the electronics of block 10 and is also the peak signal of the voltage wave form shown as 17 in FIG. 3 and on line 17 of FIG. 2. The analog division as provided herein follows computational analog computer techniques which are well established and known to those skilled in the art. Potentiometer 24 provides a convenient means for subtracting a fixed voltage from the voltage output of analog divider 23, which in this case is representative of the width of the laser beam (50 microns). The output of analog divider 23 is then passed to a time of flight output terminal 25 to provide a voltage level which is representative of the size of the cell being measured. All this is accomplished within a 40 microsecond duration of a timing gate voltage signal shown on input line 16.

In FIG. 1 biological cells to be measured are shown in laminar coaxial flow in a fluid sheath established within nozzle assembly 4, thereby causing the cells to pass through the laser beam from laser 5 one cell at a time at a relatively high rate (5,000 cells/sec). The stream of cells is passing down through the nozzle assembly 4 at a constant velocity of 10 meters/sec through the laser beam, which in the Becton Dickinson 440 is about 50 microns in width. The teaching of the present invention is that the size of the biological cell may be measured by measuring the time of flight of each of the biological cells through the laser beam. The teachings of the present invention necessarily include an electronic analog computation which has not been used before the present invention of this type of technical application. Specifically, within the time period initiated by gate pulse of 40 microseconds appearing at input line 16 of FIG. 2, a voltage pulse is generated by the forward light scatter measured by collector 6 or the secondary emission measured by the photomultiplier tubes 7 or 8 representing the total light received, and that pulse appears on line 17 of FIG. 2 and is represented by wave form 17' of FIG. 3 and is hereafter referred to as a first electrical signal from the low forward light scatter or secondary fluorescent emission derived from a single cell as it passes through the broader laser beam. That signal is then used in FIG. 2 to derive a second electrical signal having an amplitude determined by the time integral of the first electrical signal with the time integral being generated by a combination of operational amplifier 21 and capacitor 20 and resistor 26. Capacitor 20 remains in the circuit for the time period determined by the gating voltage wave form 16' of FIG. 3. This gate uses electronic switch 19, which is of conventional construction, and the second electrical signal representing the time integral of the first electrical signal is applied via line 22 to energize an analog divider 23 at its numerator input 7, while at the same time having at its divisor input 10 a third electrical signal having an amplitude equal to the peak amplitude of said first electrical signal. The output of said analog divider component 23 would thereby derive a fourth electrical signal by dividing the said second electrical signal by said third electrical signal, thereby deriving an electrical signal commensurate with the width of each of said biological cells plus the width of the laser beam. The fifth electrical signal proportional to the width of said biological cell is then derived at output terminal 25 by utilizing a negatively energized potentiometer 24 as an input to the analog divider with the output of said negatively energized potentiometer 24 being utilized for subtracting from said fourth electrical signal a constant electrical signal proportional to the width of the laser beam (in this case 50 microns).

The circuit of FIG. 2 contains other necessary components. They include diodes and resistors as shown. Diode 27 may be in this specific circuit an IN34 and function to set a threshold for generation of signal wave form 17'. The input resistor adjacent thereto measures 10K ohms and functions as part of the time constant of the integrator. The electronic switch 19 is one half of a model DG200 made by Siliconix Inc. The output resistance for the electronic switch is 100 ohms to avoid large currents. The integrating capacitor is 0.001 ufa-rads. The operational amplifier 21 is a model LF356 made by National Semiconductor Inc. The analog divider 23 is a model AD534JH made by Analog Device Inc. The output of the analog divider is passed to the output terminal via semiconductor diode IN914. The output terminal is maintained above ground by a 10K load resistor.

As set forth above, the teachings of the present invention relate to the use of above computational techniques for sampling and calculating the time it takes for the biological cell being measured to pass at a constant velocity across a larger light beam by following the computational technique. A more accurate measurement of the size of the biological cell is made, and the magnitude of that signal and a size measurement may be used to initiate the operation of the sorting function of the cytometer through an emitter follower 28 and analog-to-digital converter 31 made by Nuclear Data Inc. as model MD576 to energize the deflection plates appropriately to sort the cells one at a time in different collecting containers based on an accurate measurement of their size. The precise nature of the circuitry for doing this is not a critical part of the present invention, and the circuitry and components shown in block 32 are intended to cover those components that are present in the Becton Dickinson 440 or equivalent components in other equipment made by others utilizing the teachings of the present invention.

Referring to FIG. 3, wave form 16' shows the gating voltage providing the timing for the arithmetic operation which is synchronized through means not shown herein using standard techniques to coincide with and be initiated by light sensitive means at the time of the precise entry of the biological cell (being measured) into the field of the laser light beam. Wave form 17' shows the voltage level generated by light energy impinging on the low angle forward scatter collector 6 or secondary emission fluorescent signal impinging on photomultiplier tube 7 or the secondary emission fluorescent signal impinging on photomultiplier tube 8. Wave form 18' shows the voltage level representing the peak amplitude of the output of the scatter collector 6 or the photomultiplier tubes 7 and 8 commensurate with the peak amplitude either from light scatter or a secondary fluorescent emission respectively. Wave form 22' represents the instantaneous time integral of input signal 17'. Wave form 25' represents a signal commensurate with the amplitude of wave form 22' divided by the instantaneous amplitude of wave form 18', which in turn is commensurate with the width of the biological cell under examination. The width of the laser beam is subtracted from the voltage wave form of wave form 25' by the negative voltage source of negatively energized potentiometer 24, which has a setting based upon the width of the laser beam (in this case 50 microns).

It is fundamental to the teachings of the present invention that the aforesaid electrical wave form 22 be a time integral of the first signal between thresholds to avoid false triggers and eliminate noise. The threshold is set by the turn on level of diode 27. These two thresholds are fixed at 0.3 volts by the 1N34.

A practical application of the time-of-flight program for measuring nuclear size is illustrated by experiments recently performed by researchers with the support of the teachings of the present invention in that the nuclei of the cells were measured for DNA content based on the magnitude of the fluorescence of a DNA-specific dye, and the size of the nuclei and amount of the DNA were deemed equivalents. They were studying the genetic makeup of unisexual hybrids of the minnows *Phloxinus eos* and *Phloxinus neogaeus*. These creatures are all female parthenogenes and include both diploid and triploid forms (Vrijenhoek, R. C. in *Evolutionary Genetics of Fishes* B. J. Turner, ed., Plenum Press, New York 1984, p. 399). Flow cytometric analysis of DNA was used to (1) rapidly sort individual fish cells by ploidy, and (2) analyze the distribution of ploidy levels in mosaics. Cells stained with DAPI, a DNA-specific dye fluorescing at 425 nm (Utter, F. M., O. W. Johnson, G. H. Thorgaard, and P. S. Rabinovitch in *Agriculture* 35:125, 1983). The intensity of fluorescence provides a measure of DNA.

Figure 4A:
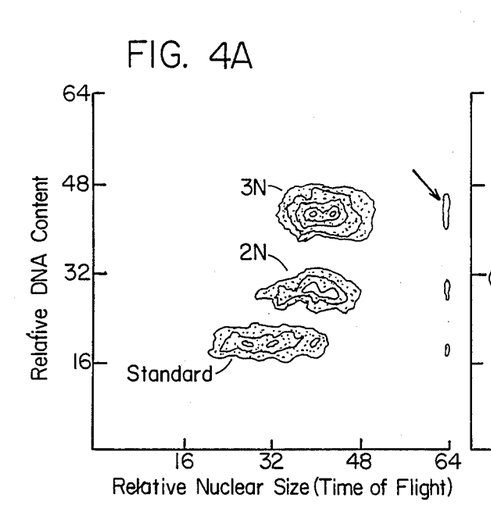
FIGS. 4A and 4B are computer displays showing how the application of the teachings of the present invention to the measurement of the size of the nucleus of cells as they pass through a larger laser beam may be used to discriminate between distributive groups of both diploid and triploid cells based on nuclear size (in this case related to DNA content). The contoured objects in FIGS. 4A and 4B represent nuclear size (DNA) distributions of many cells, when 3N are triploid, 2N are diploid, and "standard" represents a known DNA content of the nuclei of groups of cells.
Figure 4B:
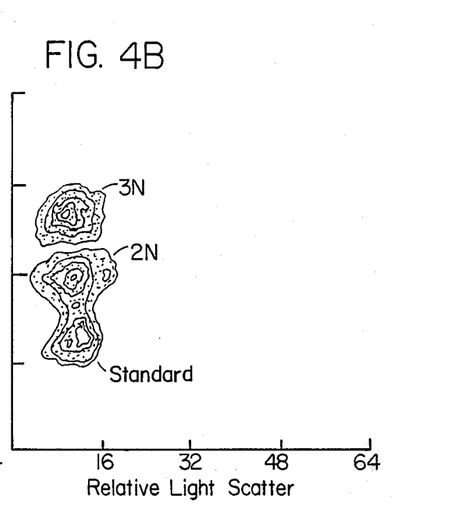

Data analysis was performed by computer 12 of FIG. 1 by plotting DAPI fluorescence (linear scale) vs. either time-of-flight at 425 nm (FIG. 4A) or forward light scatter (FIG. 4B). The time-of-flight analysis has two advantages. (1) It more accurately represents nuclear size. The mean time-of-flight value for triploid nuclei is noticeably greater than that for diploid nuclei. This had been confirmed by direct microscopic measurement. Note in FIG. 4A that cells of larger DNA content are bigger (farther to right) as measured by time-of-flight circuit, while on the light scatter axis, FIG. 4B, no correlation between DNA content and scatter is seen. Note also that the contoured objects shown in FIG. 4A, B represent distributions of many cells, where 3N are triploid, 2N are diploid, and "standard" represents a known DNA content group of cells. (2) Clumped nuclei are readily distinguised along the time-of-flight axis and can easily be deleted by editing, yielding more accurate means values for DNA content. Separation is especially important when one of the two ploidy levels in a mosaic is represented by a small population of cells and is obscured by clumped nuclei. In FIG. 4A the clumped cells can barely be seen at the right edge (arrow), while in 4B they are directly superimposed and indistinguishable. The computer used in the presentation provided in FIG. 4A and 4B was a Digital Equipment Company Inc. model 11/23.

Fluorescence is a phenomenon where light energy of one color is absorbed and light energy of a different color is emitted. Examples: Blue absorbed, green emitted and yellow absorbed, red emitted. Fluorescence Activated Cell Sorters are a type of automatic Fluorescence Microscopy. In conventional fluorescence microscopy, cells are placed on a glass slide and viewed with a microscope through a suitable emission filter. The cells are typically analyzed for the presence or absence of fluorescent emissions resulting from excitation with light of the proper color. The excitation light source is usually incandescent and is focused on the slide via suitable filters to give the proper excitation color. In the FACS, a coaxial flow system with a cell suspension as the center fluid component is generated. A coaxial flow system is one formed with concentric layers or multiple unmixed stream components. The FACS fluid system has two layers. The inner one forms the core of a 50 micron diameter stream. It is approximately 10 microns in diameter and contains sample fluid with suspended cells. The outer stream component is called the sheath and is sometimes PBS (Phosphate Buffered Saline). This fluid stream is passed through a focused single color laser beam at about 10 meters per second. As cells pass through the laser beam, light pulses are emitted which are directed through focusing lenses and appropriate filters to photodetectors. The photodetectors convert the optical energy into an electrical current pulse with amplitude proportional to light intensity. The resulting current pulses are then coupled into a data analysis system for classification and processing. This flow/measurement technology results in a system capable of processing thousands of cells per second and also has much better measurement accuracy when the teachings of the present invention are used.

The FACS unit includes a cell sorting feature which is not available in conventional fluorescence microscopes. For sorting, the coaxial stream forming nozzle is mounted in a piezoelectric crystal that is ultrasonically vibrated at 35–40,000 cycles per second. The vibrations cause the coaxial stream to form drops at a distance of three millimeters below the point where the laser intersects the stream (that is about 0.25 mm below the nozzle). The stream of droplets continues and passes between two plates charged with several kilovolts. After cell optical characteristics are measured and classified and a time delay which allows the cell to travel to the droplet forming point, drops which contain cells are charged positive or negative and deflected left or right by the electric field while uncharged drops are not deflected.

The foregoing description has been directed to particular embodiments of the invention in accordance with the requirements of the Patent Statutes for the purpose of illustration and explanation. It will be apparent, however, to those skilled in this art that many modifications and changes will be possible without department from the scope and spirit of the invention. It is intended that the following claims be interpreted to embrace all such modifications and changes.

We claim:

1. A new and improved method of measuring the size of a biological cell in a flow cytometer, comprising the steps of:
1. Directing said biological cells in column flow at a constant velocity;
2. Passing a laser beam having a cross section larger than each of said cells through said biological cells in column flow so that only one biological cell passes through said laser beam at a time;
3. Measuring the time of flight of each said biological cell through said laser beam deriving an electrical signal commensurate with the width and/or volume of each said biological cell by
   a. deriving a first electrical signal from the low angle forward light scatter characteristic or secondary fluorescent emission from a single cell as it passes through the said laser beam;
   b. deriving a second electrical signal having an amplitude determined by the time integral of said first electrical signal;
   c. deriving a third electrical signal having an amplitude equal to the peak (maximum) amplitude of said first electrical signal;
   d. deriving a fourth electrical signal by dividing the said second electrical signal by the said third electrical signal therefore deriving an electrical signal commensurate with the width of each said biological cell plus the width of the laser beam;
   e. deriving a fifth electrical signal by subtracting from said fourth electrical signal a constant electrical signal proportional to the width of the said laser beam whereby the fifth electrical signal is directly proportional to the width of said biological cell.

2. A new and improved flow cytometer means for measuring the size of a biological cell, comprising:
1. Means for directing said biological cells in column flow at a constant velocity;
2. Means for passing a laser beam having a cross section larger than each of said cells through said biological cells in column flow so that only one biological cell passes through said laser beam at a time;
3. Means for measuring the time of flight of each said biological cell through said laser beam deriving an electrical signal commensurate with the width and/or volume of each said biological cell or its nucleus, comprising:
   a. means for deriving a first electrical signal from the low angle forward light scatter characteristic or secondary fluorescent emission from each cell as it passes through the said laser beam;
   b. means for deriving a second electrical signal having an amplitude determined by the time integral of said first electrical signal;
   c. means for deriving a third electrical signal having an amplitude equal to the peak amplitude of said first electrical signal;
   d. means for deriving a fourth electrical signal by dividing the said second electrical signal by the said third electrical signal therefore deriving an electrical signal commensurate with the width of each said biological cell plus the width of the laser beam;
   e. means for deriving a fifth electrical signal by subtracting from said fourth electrical signal a constant electrical signal proportional to the width of the laser beam whereby the fifth electrical signal is directly proportional to the width of said biological cell.

3. The new and improved flow cytometer means of claim 2 wherein electrical sorting means are connected to the output of said means for deriving said fifth electrical signal to sort and collect each cell based on the magnitude of said fifth electrical signal.

4. The new and improved flow cytometer means of claim 3 wherein a computer is also connected to the output of said means for deriving said fifth electrical signal.

5. A new and improved flow cytometer means for measuring the size of a biological cell, comprising:
1. Means for directing said biological cells in column flow at a constant velocity;
2. Means for passing a laser beam having a cross section larger than each of said cells through said biological cells in column flow so that only one biological cell passes through said laser beam at a time;
3. Means for measuring the time of flight of each said biological cell through said laser beam deriving an electrical signal commensurate with the width and/or volume of each said biological cell or its nucleus, comprising:
   a. means for deriving a first electrical signal from the secondary fluorescent emission from each cell as it passes through the said laser beam;
   b. means for deriving a second electrical signal having an amplitude determined by the time integral of said first electrical signal;
   c. means for deriving a third electrical signal having an amplitude equal to the peak amplitude of said first electrical signal;
   d. means for deriving a fourth electrical signal by dividing the said second electrical signal by the said third electrical signal therefore deriving an electrical signal commensurate with the width of each biological cell plus the width of the laser beam;
   e. means for deriving a fifth electrical signal by subtracting from said fourth electrical signal a constant electrical signal proportional to the width of the laser beam whereby the fifth electrical signal is directly proportional to the size of nucleus or cytoplasm of said biological cell.

6. The new and improved flow cytometer means of claim 5 wherein electrical sorting means are connected to the output of said means for deriving said fifth electrical signal to sort and collect each cell based on the magnitude of said fifth electrical signal.

7. The new and improved flow cytometer means of claim 6 wherein a computer is also connected to the output of said means for deriving said fifth electrical signal.

8. A new and improved flow cytometer means for measuring the size of a biological cell, comprising:
1. Means for directing said biological cells in column flow at a constant velocity;
2. Means for passing a laser beam having a cross section larger than each of said cells through said biological cells in column flow so that only one biological cell passes through said laser beam at a time;
3. Means for measuring the time of flight of each said biological cell through said laser beam deriving an electrical signal commensurate with the width and/or volume of each said biological cell, comprising:
   a. means for deriving a first electrical signal from the low angle forward light scatter characteristic from each cell as it passes through the said laser beam;
   b. means for deriving a second electrical signal having an amplitude determined by the time integral of said first electrical signal;
   c. means for deriving a third electrical signal having an amplitude equal to the peak amplitude of said first electrical signal;
   d. means for deriving a fourth electrical signal by dividing the said second electrical signal by the said third electrical signal therefore deriving an electrical signal commensurate with the width of each said biological cell plus the width of the laser beam;
   e. means for deriving a fifth electrical signal by subtracting from said fourth electrical signal a constant electrical signal proportional to the width of the laser beam whereby the fifth electrical signal is directly proportional to the width of said biological cell.

9. The new and improved flow cytometer means of claim 8 wherein electrical sorting means are connected to the output of said means for deriving said fifth electrical signal to sort and collect each cell based on the magnitude of said fifth electrical signal.

10. The new and improved flow cytometer means of claim 9 wherein a computer is also connected to the output of said means for deriving said fifth electrical signal.

* * * * *